US00PP29243P2

(12) United States Plant Patent
Nebelmeir

(10) Patent No.: US PP29,243 P2
(45) Date of Patent: Apr. 17, 2018

(54) POINSETTIA PLANT NAMED 'LAZZPO1319'

(50) Latin Name: ***Euphorbia pulcherrima* Willd.**
Varietal Denomination: LAZZPO1319

(71) Applicant: Johannes Nebelmeir, Marling (IT)

(72) Inventor: Johannes Nebelmeir, Marling (IT)

(73) Assignee: Lazzeri Societa Agricola a.r.l., Sabaudia (IT)

( * ) Notice: Subject to any disclaimer, the term of this patent is extended or adjusted under 35 U.S.C. 154(b) by 0 days.

(21) Appl. No.: 15/530,655

(22) Filed: Feb. 16, 2017

(51) Int. Cl.
*A01H 5/02* (2006.01)

(52) U.S. Cl.
USPC ..... Plt./304

(58) Field of Classification Search
USPC ..... Plt./304, 305
CPC ..... A01H 5/0244
See application file for complete search history.

*Primary Examiner* — Kent L Bell
(74) *Attorney, Agent, or Firm* — C. A. Whealy

(57) ABSTRACT

A new and distinct cultivar of Poinsettia plant named 'LAZZPO1319', characterized by its upright and uniformly mounding plant habit; vigorous growth habit; freely branching habit; oak leaf-shaped, dark green-colored leaves; large and full inflorescences with oak leaf-shaped flower bracts that are very light yellow appearing close to white in color; and excellent post-production longevity.

2 Drawing Sheets

Botanical designation: *Euphorbia pulcherrima* Willd.
Cultivar denomination: 'LAZZPO1319'.

BACKGROUND OF THE INVENTION

The present invention relates to a new and distinct cultivar of Poinsettia plant, botanically known as *Euphorbia pulcherrima* Willd. and hereinafter referred to by the name 'LAZZPO1319'.

The new Poinsettia plant is a product of a planned breeding program conducted by the Inventor in Merano, Italy. The objective of the breeding program is to create new upright and freely-branching Poinsettia plants with white-colored flower bracts.

The new Poinsettia plant originated from a polycross made by the Inventor in 2010 in Merano, Italy of an unidentified proprietary selection of *Euphorbia pulcherrima* Willd., not patented, as the female, or seed, parent with mixed pollen from a number of *Euphorbia pulcherrima* Willd. proprietary selections and commercial varieties with white-colored flower bracts as the male, or pollen, parent. The new Poinsettia plant was discovered and selected by the Inventor as a single flowering plant within the progeny of the stated polycross in a controlled greenhouse environment in Merano, Italy in December, 2011.

Asexual reproduction of the new Poinsettia plant by terminal vegetative cuttings in a controlled greenhouse environment in Merano, Italy since May, 2012 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'LAZZPO1319'. These characteristics in combination distinguish 'LAZZPO1319' as a new and distinct Poinsettia plant:

1. Upright and uniformly mounding plant habit.
2. Vigorous growth habit.
3. Freely branching habit.
4. Oak leaf-shaped, dark green-colored leaves.
5. Large and full inflorescences with oak leaf-shaped flower bracts that are very light yellow appearing close to white in color.
6. Excellent post-production longevity.

Plants of the new Poinsettia can be compared to plants of the female parent selection. Plants of the new Poinsettia differ primarily from plants of the female parent selection in plant performance as plants of the female parent selection are not suitable for typical commercial greenhouse Poinsettia production.

Plants of the new Poinsettia can be compared to plants of *Euphorbia pulcherrima* Willd. 'Duegla13', disclosed in U.S. Plant Pat. No. 26,094. In side-by-side comparisons, plants of the new Poinsettia differ primarily from plants of 'Duegla13' in the following characteristics:

1. Leaves of plants of the new Poinsettia are darker green in color than leaves of plants of 'Duegla13'.
2. Leaves and flower bracts of plants of the new Poinsettia are oak leaf-shaped whereas leaves and flower bracts of plants of 'Duegla13' are more rounded.
3. Flower bracts of plants of the new Poinsettia are "whiter" in color than flower bracts of 'Duegla13'.

Plants of the new Poinsettia can be compared to plants of *Euphorbia pulcherrima* Willd. 'OGLPNT14001', disclosed in U.S. Plant Pat. No. 21,715. In side-by-side comparisons, plants of the new Poinsettia differ primarily from plants of 'OGLPNT14001' in the following characteristics:

1. Leaves of plants of the new Poinsettia are darker green in color than leaves of plants of 'OGLPNT14001'.
2. Leaves and flower bracts of plants of the new Poinsettia are oak leaf-shaped whereas leaves and flower bracts of plants of 'OGLPNT14001' are more rounded.
3. Plants of the new Poinsettia flower earlier than plants of 'OGLPNT14001'.
4. Flower bracts of plants of the new Poinsettia are "whiter" in color than flower bracts of 'OGLPNT14001'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet comprises a side perspective view of a typical flowering plant of 'LAZZPO1319' grown in a container.

The photographs on the second sheet are close-up views of a typical inflorescence and the upper and lower surfaces of transitional and fully expanded flower bracts of 'LAZZPO1319'.

DETAILED BOTANICAL DESCRIPTION

The aforementioned photographs and following observations and measurements describe plants grown during the summer to winter in 15-cm containers in a glass-covered greenhouse in Merano, Italy and under cultural practices typical of commercial Poinsettia production. During the production of the plants, day temperatures ranged from 15° C. to 20° C., night temperatures ranged from 10° C. to 15° C. and light levels ranged from 40 to 55 klux. Plants were pinched one time two weeks after planting and were five months old when the photographs and the detailed description were taken. In the following description, color references are made to The Royal Horticultural Society Colour Chart, 1995 Edition, except where general terms of ordinary dictionary significance are used.

Botanical classification: *Euphorbia pulcherrima* Willd. 'LAZZPO1319'.

Parentage:

*Female, or seed, parent.*—Unidentified proprietary selection of *Euphorbia pulcherrima* Willd., not patented.

*Male, or pollen, parent.*—Mixed pollen from a number of *Euphorbia pulcherrima* Willd. proprietary selections and commercial varieties with white-colored flower bracts.

Propagation:

*Type.*—Terminal vegetative cuttings.

*Time to initiate roots, summer.*—About two weeks at soil temperatures ranging from 22° C. to 25° C. and ambient temperatures ranging from 25° C. to 30° C.

*Time to produce a rooted young plant, summer.*—About four weeks at soil temperatures ranging from 22° C. to 25° C. and ambient temperatures ranging from 25° C. to 30° C.

*Root description.*—Medium to thick, slightly fleshy; typically pale creamy white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright and uniformly mounded plant habit; inverted triangle with rounded crown; large full inflorescences positioned above the foliar plane; vigorous growth habit and moderate to rapid growth rate.

*Plant height, soil level to top of floral plane.*—About 28 cm.

*Plant diameter or spread.*—About 45 cm.

*Lateral branch description.*—Branching habit: Freely branching habit with about six to eight lateral branches developing after pinching. Length: About 25 cm. Diameter: About 5 mm. Internode length: About 8 mm to 18 mm. Strength: Strong. Texture and luster: Smooth, glabrous; glossy. Color: Close to 137B; color becoming closer to 199D with development.

*Leaf description.*—Arrangement: Alternate, simple. Length: About 10 cm to 12 cm. Width: About 8 cm to 9.5 cm. Shape: In outline, roughly ovate; oak leaf-shaped. Apex: Acuminate. Base: Cuneate. Margin: Lobed with typically two medium to deep lobes. Venation pattern: Pinnate. Texture and luster, upper surface: Smooth, glabrous; moderately glossy. Texture and luster, lower surface: Smooth, glabrous; matte. Color: Developing leaves, upper surface: Close to 144A. Developing leaves, lower surface: Close to 146B to 146C. Fully expanded leaves, upper surface: Close to 136A; venation, close to 146B. Fully expanded leaves, lower surface: Close to 137B; venation, close to 146C. Petioles: Length: About 3 cm to 5 cm. Diameter: About 2.5 mm. Strength: Moderately strong. Texture and luster, upper and lower surfaces: Smooth, glabrous; glossy. Color, upper surface: Close to 146C. Color, lower surface: Close to 146D.

Inflorescence description:

*Inflorescence type and habit.*—Large full inflorescences are compound corymbs of cyathia with colored flower bracts subtending the cyathia; one inflorescence per lateral branch with inflorescences positioned above and beyond the foliar plane.

*Fragrance.*—None detected.

*Natural flowering season.*—Plants flower naturally during the late autumn to winter under long nyctoperiod conditions; inflorescence initiation and development can be induced under artificial long nyctoperiod conditions; response time is about 8 to 8.5 weeks.

*Post-production longevity.*—Excellent post-production longevity; plants of the new Poinsettia maintain good substance and bract color for about four to six weeks; flower bracts persistent.

*Inflorescence width.*—About 25 cm.

*Inflorescence height.*—About 2.5 cm.

*Flower bracts.*—Quantity per inflorescence: About 15. Length: About 9.5 cm to 11 cm. Width: About 6.5 cm to 8.5 cm. Shape: In outline, roughly ovate; oak leaf-shaped. Apex: Acuminate. Base: Obtuse. Margin: Lobed with typically two medium to deep lobes. Aspect: Horizontal to slightly declined. Venation: Pinnate. Texture and luster, upper and lower surfaces: Moderately rugose, glabrous; matte. Color: Developing bracts, upper surface: Close to 8D. Developing bracts, lower surface: Close to 8C. Fully expanded bracts, upper surface: Close to 11D; venation, close to 11D; color becoming closer to 11C with development. Fully expanded bracts, lower surface: Close to 10D; venation, close to 10D; color does not change with development. Bract petioles: Length: About 1.8 cm. Diameter: About 2 mm. Texture and luster, upper and lower surfaces: Smooth, glabrous; glossy. Color, upper surface: Close to 149B. Color, lower surface: Close to 150C.

*Cyathia*.—Quantity per corymb: About seven to ten. Length: About 6 mm. Width: About 5 mm. Shape: Ovate to spherical. Texture and luster, inner and outer surfaces: Smooth, glabrous; matte. Color, developing, inner and outer surfaces: Close to 144A. Color, fully developed, inner surface: Close to 144D. Color, fully developed, outer surface: Close to 144C. Nectaries: Quantity per cyathium: Typically one or two. Length: About 4 mm. Diameter: About 2 mm. Shape: Lip-shaped. Texture and luster, inner and outer surfaces: Smooth, glabrous; matte. Color, fully developed, inner surface: Close to 12A. Color, fully developed, outer surface: Close to 9B.

*Pedicels*.—Length: About 1 mm to 2 mm. Diameter: About 1 mm. Strength: Moderately strong. Texture and luster: Smooth, glabrous; glossy. Color: Close to 144C.

*Reproductive organs*.—Stamens: Quantity per cyathia: About 20. Filament length: About 2 mm to 3 mm. Filament color: Close to 155D. Pistils: Quantity per cyathia: About three. Pistil length: About 3 mm to 4 mm. Style length: About 2 mm to 3 mm. Style shape: Recurved. Fruits: Quantity: None to very few with none to three seeds. Length: About 8 mm to 12 mm. Diameter: About 6 mm to 10 mm. Texture: Smooth, glabrous.

Pathogen & pest resistance: Plants of the new Poinsettia have not been shown to be resistant to pathogens and pests common to Poinsettia plants.

It is claimed:

1. A new and distinct Poinsettia plant named 'LAZZPO1319' as illustrated and described.

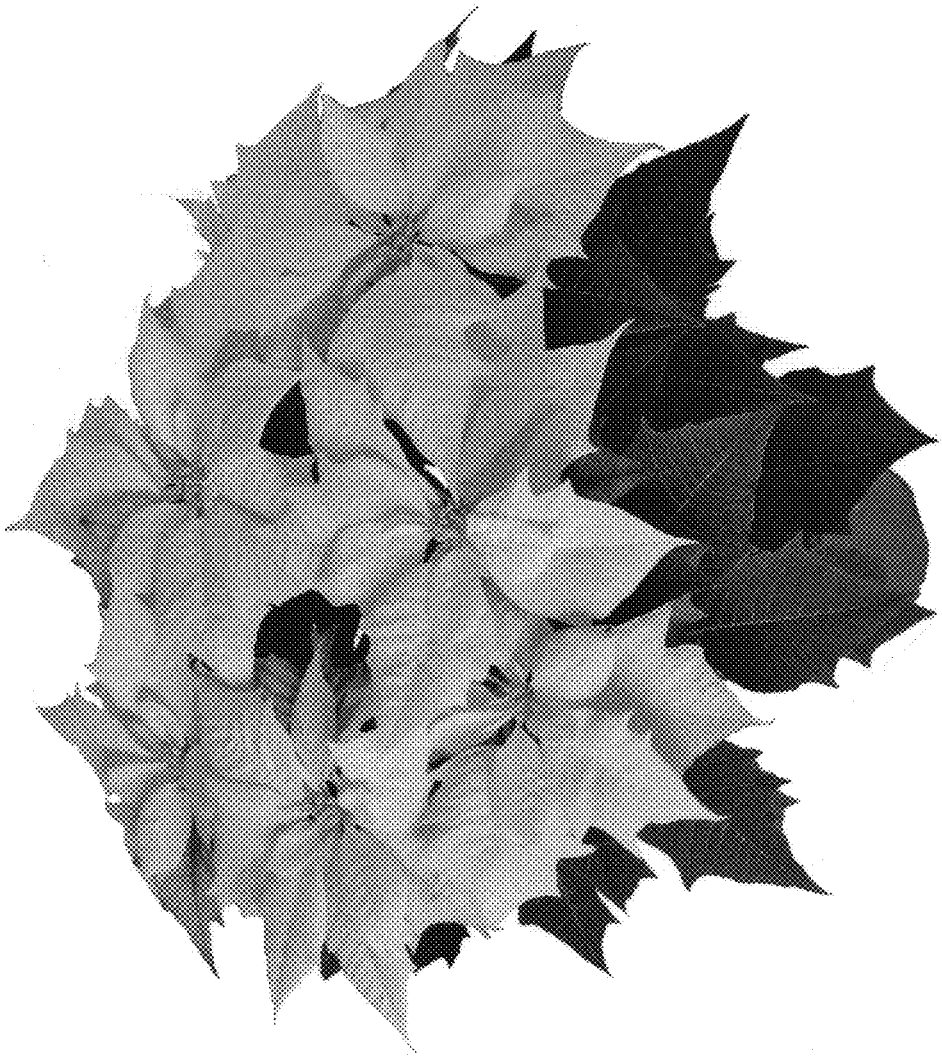

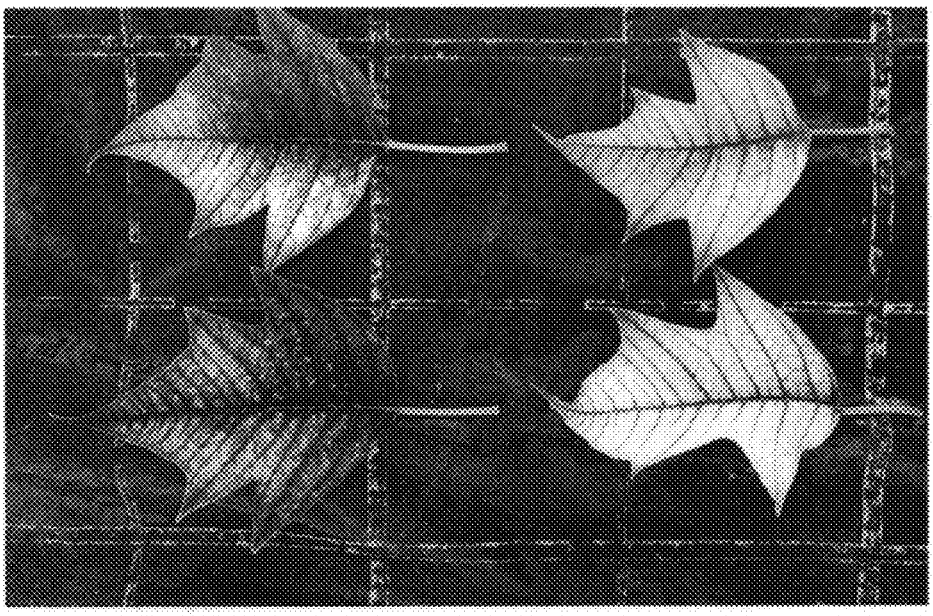
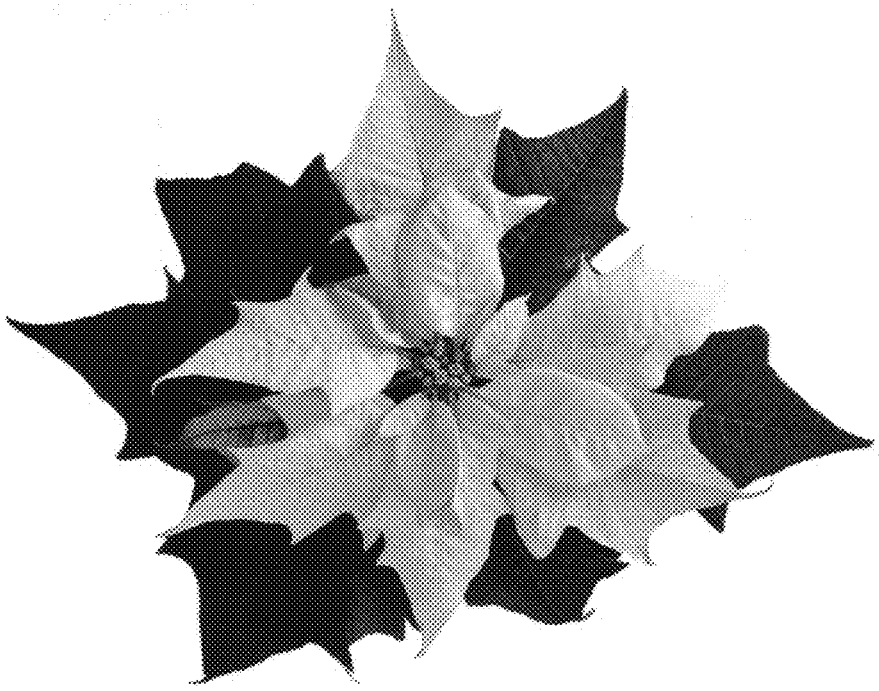

* * * * *